US005698474A

United States Patent [19]
Hurley

[11] Patent Number: 5,698,474
[45] Date of Patent: Dec. 16, 1997

[54] HIGH SPEED DIAMOND-BASED MACHINING OF SILICON SEMICONDUCTOR DIE IN WAFER AND PACKAGED FORM FOR BACKSIDE EMISSION MICROSCOPE DETECTION

[75] Inventor: Daniel T. Hurley, San Ramon, Calif.

[73] Assignee: Hypervision, Inc., Fremont, Calif.

[21] Appl. No.: 606,638

[22] Filed: Feb. 26, 1996

[51] Int. Cl.$^6$ ............................................. H01L 21/461
[52] U.S. Cl. ........................... 437/249; 437/209; 437/974; 148/DIG. 135
[58] Field of Search ................... 437/209, 211, 437/214, 217, 218, 219, 220, 902, 974, 249; 148/DIG. 135

[56] References Cited

U.S. PATENT DOCUMENTS

| | | | |
|---|---|---|---|
| 5,155,068 | 10/1992 | Tada | 437/211 |
| 5,242,862 | 9/1993 | Okabe et al. | 437/225 |
| 5,273,940 | 12/1993 | Sanders | 437/217 |
| 5,354,717 | 10/1994 | Pollock et al. | 437/974 |
| 5,369,058 | 11/1994 | Burns et al. | 437/209 |
| 5,424,254 | 6/1995 | Damiot | 437/974 |
| 5,504,036 | 4/1996 | Dekker et al. | 437/974 |
| 5,585,661 | 12/1996 | McLachlan et al. | 437/974 |

OTHER PUBLICATIONS

Adams, "Backside-Thinned Emission Imaging of Packaged Devices and Wafers", Asian Electronics Engineer, Oct. 1996.

Cambra, "Finding Functional Failures Via Docking Emission Microscopy", Asian Electronics Engineer, Dec. 1995.

Adams, "Backside Inspection Reveals Hidden Defects", Electronic Production/Test Inspection Supplement, Nov. 1996.

Adams, "IC Failure Analysis Using Real–Time Emission Microscopy," Semiconductor International, no date.

Adams, "Emission Microscopes Reveal IC Defects," Test & Measurement World, Feb. 1995.

Adams, "Backside Inspection", European Semiconductor, Oct. 1996.

Adams, "Invisible Leakage Detected Via Microsopy Technique", Solid State Technology, Nov. 1994.

*Primary Examiner*—Kevin Picardat
*Attorney, Agent, or Firm*—Townsend and Townsend and Crew LLP; Henry K. Woodard

[57] ABSTRACT

Emission microscopy testing of semiconductor integrated circuits is accomplished from the back side of a packaged die or a wafer but selectively milling the back surface using high speed (e.g., 40,000–60,000 rpm) milling tool having a 150 grit 0.125 inch diameter laterally translated at 3 inches per minute and taking cuts up to approximately 0.00025 inch (6 microns). In milling a packaged die, a trench is first milled in the molding material holding the die in the package and surrounding the die so that the tool can momentarily pause to switch directions off the die face. The die or wafer can be thinned to less than 200 microns for the emission microscopy testing.

16 Claims, No Drawings

HIGH SPEED DIAMOND-BASED MACHINING OF SILICON SEMICONDUCTOR DIE IN WAFER AND PACKAGED FORM FOR BACKSIDE EMISSION MICROSCOPE DETECTION

FIELD OF THE INVENTION

This invention relates generally to the field of testing semiconductor circuits and more particularly relates to a new method for preparing silicon semiconductors in wafer and packaged form for inspection by Emission Microscopy.

BACKGROUND OF THE INVENTION

U.S. Pat. No. 4,811,090 and earlier related U.S. Pat. Nos. 4,755,874 and 4,680,635 as well as the recently issued U.S. Pat. No. 5,475,316 disclose an image emission microscope which localizes defects in integrated circuits. The emission microscope is based on the principle of recombinant radiation. In excess current drawing conditions such as occur during semiconductor failure modes, electrons and holes in silicon, recombine and relax, giving off a photon of light which is readily detected by specialized intensified CCD sensors. The technique is widely performed by semiconductor manufacturers on wafers and delidded or decapsulated finished devices from the front side, that is looking directly down upon the surface of the integrated circuit. The predominant value of the technique is rapid detection and failure localization to the junction level of a single transistor in integrated circuits which may have up to 4,000,000 or more transistors.

The demand for greater speed in the semiconductor industry has lead to both a high level of chip integration and innovation in package design. The result of these innovations, while successful in increasing speed, has left the failure analyst with semiconductor circuits that are not inspectable using frontside inspection techniques alone for emission testing. In these circuits photons emitted from failure sites cannot reach the front side and therefore cannot be detected. Examples of the types of problems encountered include 4-5 layers of metallization, flip-chip packaging in which only the backside is presented for inspection, LOC (Lead On Chip) packaging in which the chip face is covered with metal bond pads and excessively wide metal lines or complete ground planes. In the examples cited the emissions are effectively blocked from detection or are at such low incident angle in relation to the objective lens that they are undetectable from the frontside. Since emission microscopes are routinely relied upon for failure localization the ability to continue to detect emissions from these new generation integrated circuits and new package configurations is a major concern for failure analysis. Photons from failure sites do however escape toward the back of the die as well. This has lead increasingly to the inspection of packaged semiconductor from the backside; that is, by removing the packaging, thinning the die, polishing, and then performing emission microscopy.

When emissions are produced, the light is nonisotropic going equally up to the front of the integrated circuit as well as to the back of the die silicon. Of the four known emission types, saturation, gate dielectrics, reverse bias junction avalanche and forward biasing (Latch-up), only forward-bias emissions emit with the same intensity from the backside as from the front. This predictable result is related to a narrow spectral signature from 850 nm to 1.1 um.

For the other three emission types (which are broadband emitters 550 nm to 1.1 um), the silicon acts as a filter largely absorbing the emissions occurring within the visible spectrum (400-800 nm). This silicon filter effect can be significant for weak emitters viewed from the backside. T. Ishi and K. Miyamoto in "Functional Failure Analysis Technology from Backside of VLSI Chip," Proceedings of the 20th International Symposium of Testing and Failure Analysis, Nov. 13-18, 1994, showed that the anticipated calculated absorption of silicon closely follows empirical observation:

$$I_{(x)}=(1-R)I_{(o)}exp(-ax)$$

where a=absorption coefficient
r=reflection index of silicon
x=silicon thickness
$I_{(o)}$=initial IR strength at the surface
$I_{(x)}$=escaping IR strength Given that semiconductor die are upwards of 750 um (33.8 mils) thick, it can be calculated that for a die thinned to 340 um thickness wavelengths of about 1000 nm are required. Empirical observation has corroborated that no emission is seen below 950 nm confirming the silicon filter effect. For gate dielectric failure which can be especially weak, the need for thinning samples to optimize detection sensitivity is clear. In "Infrared Emission Microscope Analyzes Defects in Multilevel LSI and Silicon Bulk," Toshiba Corporation, Nikkei Electronics Asia, September 1992, Kazuhiko Etoh performed photon count evaluations from the front and rearside for all known emission types without thinning the backside silicon. For light emitted from a saturated pn junction of an npn transistor (intensity) photon counts dropped by 2 orders of magnitude. Similarly, gate dielectric for MOS transistors dropped by two orders of magnitude and reverse bias between the emitter and base or between collector and base resulted in a 3 order of magnitude drop in detection sensitivity. As anticipated, there was no loss in photon count from forward biased emissions since these occur in the 850–11 nm range and are largely above the silicon filter effect.

Joseph and Berry evaluated the effects of heavily doped P+ silicon which is receiving wider usage in advanced logic and microprocessor applications in "Infrared Laser Microscopy of Structures on Heavily Doped Silicon," IBM Proceedings of the 18th International Symposium of Testing and Failure Analysis, Oct. 17-24, 1992. For a 625 um thick die P– not heavily doped wafers transmit over 50% of their light while P+ wafers of similar thickness transmit only a maximum of only 1-2% over a very narrow range around the silicon bandgap at 1.1 um. In an effort to improve performance, they planar lapped and thinned the die to reduce the silicon filter effect and improve illuminated image quality.

Prior art in preparing samples for backside inspection has evolved over the past three years but largely has not been widely utilized largely due to considerable drawbacks in the techniques. These techniques include:

A. Planar lapping with diamond slurries. In integrated packages such as plastic encapsulated devices backthinning is achieved by bending the leads out and up and lapping through the packaging, leadframe and die. With the die exposed, the analyst must estimate the material removed. Once thinned, the leads can never be reformed and the package can never be socket tested. For high lead count devices this is a considerable hardship. The lead pitch being exceptionally small on high pin count devices, the process of bending the leads back can often result in complete lead fracture and separation where it meets the packaging. For DIP (dual in-line packages) the leadframe may be ground away with the die.

Thinning of wafers can also be easily achieved using this technique but with considerable drawback. Planar lapping refers to lapping the entire wafer to reduce the bulk property of the silicon by several hundred microns. A 750 um thick wafer would need to be lapped to less than 200 um (preferably less than 100 um) to reduce the silicon absorption effect. An 8" (200 mm) wafer thinned to this level is exceptionally brittle and presents a real obstacle for inspection as the mechanical force needed to clamp and probe the wafer with a probe card is sufficient force to induce cracking.

B. Reagent thinning. The use of etching compounds and reagents based on Hydrofluoric acid have been utilized. Hydrofluoric Acid will dissolve silicon neatly but is exceptionally hazardous. It is one of the few known acids to eat away skin and tissue down to the bone. It is very undesirable to use on a routine basis for that reason. The liability with continued usage is high even in a controlled environment making it impractical for day to day FA usage.

C. Dimpling. Dimpling was developed for TEM (tunneling electron microscopy) and is a slow speed grinding operation using a weighted head diamond wheel turning at low RPM. As the wheel spins above the part below is spun at low RPM as well. This results in a bowl shaped cut known as a dimple. The flat area is directly under the wheel. If the diamond wheel is perpendicular and centered to the device as a dimple is produced having radiused side walls and a flat spot equivalent to the thickness of the grinding wheel. Final polishing is done with diamond slurries or pastes to achieve a mirror finish. Commercially the tool is designed for preparing small polished samples 1–3 mm in size. Die sizes today are reaching 20 mm and larger. The radium edge of the cut is a problem as the slope of remaining silicon acts as a filter. The inspection area is limited with regions outside of the flatspot abruptly losing contrast due to increasing silicon thickness. The technique is also time consuming as the low RPM tool speed takes hours to cut through the packaging materials and silicon. The desired large flat area such as the entire backside of the die cannot be achieved. Preparation with this tool is similar to a boring operation rather than a backside planar preparation. It is not possible to prepare a part without a radiused edge. For users concerned with detecting where the emission might occur at any point over a large die surface the technique is limited to boring "test hole" over increasingly larger areas of the part.

D. Ion Milling. Focused Ion Beam (FIB) systems have been widely utilized to selectively mill semiconductors. They work in a high vacuum over areas generally no larger than a few microns in size. They can mill out silicon but only in a tightly defined small area. For users with detailed knowledge of the failure site they can be beneficial. The cost of FIB equipment is over $750,000. Its limited inspection window and high cost of ownership make it prohibitive for routine FA usage. As above, for users concerned with detecting where the emission might occur at any point over a large die surface the technique is limited to boring "test hole" over increasingly larger areas of the part.

E. Milling. The use of milling equipment has been utilized by the failure analyst to remove molding compound. Efforts to use machine tools for thinning the die and polishing "in package" have not been successful, leading to chipping, gouging and cracking of the die. At lower speeds and without proper technique and tooling, the dies in fact shatter even when supported by molding compound. Further, no one has attempted to even try thinning individual die on wafers which are unsupported by any molding compound. It was felt that mechanical force would shatter the wafer. This has imposed a severe limitation on the preparation of backside samples a shortcoming felt acutely by all failure analysis engineers as they attempt to deal with packages and wafers for backside inspection without a viable technique.

The present invention is directed to the testing of semiconductor integrated circuits by backside emission microscopy. The invention defines a method heretofore unseen that produces flat thinned semiconductors with a high mirror finish for inspection by an emission microscope. Many failure analysts are intimidated by the prior art and see few solutions which can be used on those parts that may need unique preparation to make them even partially inspectable. Because there is an obvious and urgent requirement for rapid detection of failure sites by emission microscopes, a rapid method for backside inspection preparation is a necessity.

The invention encompasses a high speed diamond based method of machining semiconductor wafers and packaged devices which addresses the following problems:

1. Utilizing mechanical tools of a specific kind and in a prescribed method the technique rapidly (in under one hour) produces flat, thinned and polished die ready for backside inspection utilizing mechanical tools. The entire back surface of the die is exposed, thinned and polished without cracking providing an optimum inspection window equivalent to the frontside inspection view which up to this point has not been achievable by any other method. Prior art cannot achieve this inspection window without degrading the packaging or wafer integrity.

2. The technique produces rectangular or square cuts without radiused edges in packaged devices including epoxy molding compound, aluminum oxide and copper/gold, copper tungsten or similar metal heat sink substrates.

3. The technique utilizes conventional CNC computer numerically controlled milling equipment for high precision. Accuracy in the z-axis is better than 5 microns.

4. The technique utilizes low residue non toxic cutting fluids that are not corrosive or hazardous to users or packaging materials such as leadframes.

5. The technique maintains lead integrity. The packages can be opened from the backside and the leads left undamaged. This allows them to be easily reinserted in test sockets. This is critical for high pin count fine pitch packages which are easily damaged or destroyed when the leads are bent as is required in the prior art.

6. The technique utilizes a newly developed "flipped socket" that allows inspection of the thinned die to occur in a specially designed socket that is flipped and routed away to expose the chips backsurface for inspection by the emission microscope.

7. The technique produces individual thinned die on silicon wafers. This has never been done before. Rather than thinning entire wafers, selected die on the wafer can be thinned allowing for easy clamping and inspection without fear of wafer fracture. By maintaining the wafer's bulk silicon thickness and thinning only selected die a new method has evolved for yield enhancement in the FAB environment where wafers are routinely inspected.

8. The technique provides a rapid method for in-situ backthinning of flip-chip components within their carrier packaging.

SUMMARY OF THE INVENTION

It is an objective of this invention to provide a method for successfully preparing semiconductor integrated circuits for backside inspection in both packaged form and as individual die on wafers. The technique fulfills the requirement to remove the overlying bulk of the silicon which acts as a filter effect reducing both emission detection sensitivity and image contrast in the illuminated mode. The invention addresses the shortcomings seen in prior art and does so utilizing commercially available tooling and polishing reagents in a method never before implemented The primary objectives of the invention are:

Create a window for inspection, exposing the entire backside die surface as a flat thinned and mirror polished surface for backside inspection in packaged parts and over individual die on wafers.

Effectively remove at high speed the overlying plastic molding compound and expose the backside die attach leadframe.

Remove the leadframe from the die without cratering or shattering the die.

Reduce the bulk thickness of the die to 100 um or less to overcome the silicon filter effect, without cracking the die, taking into consideration plunge pressure, feedrate and the angular edge and brittle nature of the silicon crystalline semiconductor material.

In wafers effectively reduce the bulk thickness of the wafer to 100–200 um or less over localized areas of individual die without shattering or cracking the wafer and while maintaining otherwise the mechanical integrity of the selected die and complete wafer for microprobing and mounting in a chuck assembly. This process has never been achieved before and is entirely original and has not been seen in prior art.

Effectively finish the backside surface to a mirror finish with ridges and machine marks under 5 microns. The final finishing step is critical to the final inspection and utilizes prior art diamond paste polishing techniques but in a novel manner.

The invention and objects and features thereof will be more readily apparent from the following detailed description and appended claims.

DETAILED DESCRIPTION OF PREFERRED EMBODIMENTS

In accordance with this invention an improved, safe and reliable method for preparing specimens in package and wafer form for backside inspection is presented in response to an urgent need in the semiconductor community. The technique is a departure from prior art for backside preparation of semiconductors and addresses the shortcomings of the prior art.

The steps for effective utilization of the technique are outlined below for a specific embodiment of the invention. The utilization of the invention will be readily apparent to a person with skill in the art of semiconductor yield and failure analysis.

Semiconductor Thinning Process Packaged Devices and Wafers

1. Utilizing a programmable milling machine such as an EMCO PC Mill 50 CNC milling machine the general attributes of the "pocket" (the XYZ shaped hole to be cut in the DUT (device under test)) are entered. It is also to be understood that this is a multistep process involving the changing of tools. Speed, depth, feed and coolant are all under computer control and all references made below are made with the understanding that it is achieved in a CNC (computer numerically controlled) environment. A specially built jig is used for packaged devices to hold the chip and prevent lead damage during the machining operations. This is a departure from prior art.

2. For removal of overlying bulk packaging (does not apply to wafers) a ⅛₆ twin flute end mill is utilized taking 0.005 cuts at 40,000 rpm utilizing a high speed 2 horsepower air bearing driven spindle such as NSK Planetary spindle with recirculating oil lubrication at a feed rate of 3 IPM (inches per minute) until the backside of the leadframe is exposed and the overlying material molding compound removed. The high torque capability of the tool is essential. The prior art failed in part because it did not have sufficient torque or speed to ensure clean cutting and grinding. The propensity for this to occur in packaged devices is high. Since packaged die are all slightly non-planar in relation to the packaging (the tools zero off on the package) the tooling inevitably is forced to cut into the slope of the non-planar surface. The high torque spindles can push through while high speed but lower torque spindles bind and dig in to gouge the surface. The utilization of these high speed and high torque spindles is a departure from prior art.

For ceramic packages it would require repotting of the hermetic cavity with molding compound followed by the above technique with the exception of using a diamond tipped twin flute end mill. This step is obviously omitted for wafers.

3. All cutting described is performed under a constant flood of coolant (Koolmist #378). This coolant provides three functions essential for this application. First it reduces heating by preventing the tools from heating and digging in while keeping the tool faces clean and unclogged. Second it reduces the potential for localized heat damage of the delicate semiconductor metallization, and third it reduces the potential buildup of static charges which would also damage the semiconductor metallization 4. In the development of the pocketing program a trench is cleared all the way around the entire chip. This is a crucial aspect of the technique for packaged die. Since the tooling must make successive passes and turns it was found that the momentary pause of the tool to switch direction on the die face resulted in a slight deflection (spindle compliance) which results in scoring marks and gouges at the turn points. By having the tools turn in an open area off the chip these are eliminated. This is not addressed in the prior art.

5. The leadframes (die paddle) which makes intimate contact with the die and can be bonded eutectically via gold silicon eutectic formation can crater if not handled properly. Cutting tools even at high speed tend to tear the soft copper leadframe and the resultant tearing can crater the die as the leadframe is ripped bringing with it a piece of the die. To overcome this problem a 150 grit 0.125 diameter diamond end mill grinding tool is utilized at 60,000 RPM at 3 IPM taking cuts of 0.00025 (approximately 6 um) each pass until the leadframe is ground through. The user needs to monitor this phase as the leadframe paddle can become so thin it will simply peel off which is desirable. This method significantly departs from prior art.

6. The pocket program is setup to remove the bulk quantity of the silicon using the tools speeds, plunge and feed data as above. More aggressive feeds or deeper cuts introduce significant risk to crack the die. The high speed high torque tools provide a clean cut without binding and are an essential aspect of the invention. Preparation with the 60,000 rpm grinding tools in packaged device under controlled feed conditions and under computer control are a significant departure from prior art. A large quantity of the silicon must be removed by this method to overcome the silicon filter effect. For packaged devices, thinning should reduce the bulk thickness to 100 um or slightly less. The use of 150 grit diamond is also significant as finer diamond grit while more desirable clogs rapidly and becomes quickly inefficient at grinding. In wafers the thinning should be well under 200 um. The slightly thicker die is needed to support microprobing which is unnecessary in packaged devices. To support wafers a 200 mm Teflon vacuum chuck is used to hold the wafer securely during the grinding operations.

7. To remove the machine swirl marks left by the 150 grit diamond tool a 400 grit finishing diamond end mill of 0.125 diameter (⅛") is used running at 60,000 rpm at 3 IPM taking 0.0001 cuts (plunge) in depth. Four passes is sufficient to remove most tooling marks and leaves the surface looking flat.

8. Final finishing is performed using prior art diamond pastes. Polymorphic diamond pastes are used to polish to the final mirror finish in three successive steps. These are run on the part without cooling liquids. The first and most extensive polishing is performed using the 1 um diamond paste with a soft cotton buffing wheel or end mill at 2,400 rpm until a mirror finish is achieved. It is important to continue polishing with the 1 um material for 5 minutes after the mirror finish appears to level out the 400 grit tooling marks. Two final and quick passes of 3–5 minutes each at first 0.1 micron and then 0.05 micron complete the finish. It is important to change to new buffing wheels or end mills at each change of the diamond paste.

9. Packaged devices prepared as above can be placed in specially designed socket cards referred to as "flip sockets." Since the lead are undamaged the thinned device can be reinserted in the socket for biasing. The socket mounted to its test card is specially cut to remove the area directly under the die, both the socket material and the printed circuit card material are routed away. The card is now placed in an inverted holder for inspection of the backside emissions under biasing conditions provided through the socket card. This is a departure from prior art.

10. Wafers can similarly be inspected in inverted probe stations. The advantage being the new method departs from prior art which required the entire wafer to be thinned resulting in a brittle unhandleable part. Without thinning the silicon filter effect reduces detection sensitivity. Utilizing the new technique which departs from prior art individual die can be thinned maintaining the bulk thickness of the wafer allowing both microprobing and attachment to a vacuum chuck without undo fear of shattering the wafer. This is a departure from prior art and a significant advancement for the failure analysis of wafers in the yield environment.

11. Flipped chip packaged assemblies can be opened to expose the backside of the die and then thinned and polished "in-situ" within the package without need for removal. For many configurations of flip-chip packages the new technique is the only viable non-destructive method possible for emission detection.

The described method of machining the back surface of a packaged semiconductor die or a die in a semiconductor wafer has proved to be highly successful for emission microscopy. The described tool sizes, linear speeds, and rotary speeds are preferred, but speeds within 10–15% of these speeds are satisfactory in practicing the invention. Thus, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A method of machining a back surface of a semiconductor chip to permit backside emission microscopy of an integrated circuit in a front surface of the chip, said chip affixed by molding material in a package, comprising the steps of
    a) mounting said package in a milling machine which permits movement of the package along three axes,
    b) milling molding material of said package using a rotary tool operated at a first rotary speed thereby removing molding material over the back surface and forming a trench in the molding material around the semiconductor chip, and
    c) milling semiconductor material from the back surface of the semiconductor chip using a rotary tool operating at a second rotary speed on the order of 60,000 rpm or greater.

2. The method as defined by claim 1 and further including the step of
    d) examining said semiconductor chip by backside emission microscopy.

3. The method as defined by claim 1 and further including before step c) the step of milling a lead frame die paddle on the back surface using a rotary tool operating at a speed on the order of 60,000 rpm.

4. The method as defined by claim 3 and further including the steps of
    d) removing swirl marks on the back surface after step c), and
    e) polishing the back surface with a polish paste.

5. The method as defined by claim 4 wherein step c) is completed when the semiconductor chip thickness is reduced to 200 microns or less.

6. The method as defined by claim 5 wherein step b) uses 0.005 inch cuts, the step of milling a lead frame paddle uses a 150 grit 0.125.diameter diamond end mill grinding tool traveling at 3 inches per minutes and taking 0.00025 inch each pass over the paddle, step c) uses 150 grit diamond, step d) uses 400 grit diamond end mill of 0.125 inch diameter traveling at 3 inches per minute and taking 0.0001 inch cuts in depth, and step e) uses 1 micron diamond paste with a buffing wheel at 2,400 rpm.

7. The method as defined by claim 6 and further including the step of
    f) examining said semiconductor chip by backside emission microscopy.

8. The method as defined by claim 6 wherein step e) further uses 0.1 micron diamond paste and then 0.05 micron diamond paste.

9. The method as defined by claim 1 and further including before step c) the step of milling a lead frame die paddle on the back surface using a rotary tool operating at a speed on the order of 60,000 rpm.

10. The method as defined by claim 9 and further including the steps of
    d) removing swirl marks on the back surface after step c), and
    e) polishing the back surface with a polish paste.

11. The method as defined by claim 10 wherein step c) is completed when the semiconductor chip thickness is reduced to 200 microns or less.

12. A method of selectively thinning individual die from the back surface of a semiconductor wafer having integrated circuits formed in a front surface thereby maintaining structural integrity of the wafer for backside microprobing in an unsupported environment as required for backside emission microscopy of a die comprising the steps of:

a) mounting said wafer in a milling machine which permits movement of the wafer along three axes, b) milling semiconductor from the back surface of said wafer opposite from an integrated circuit in the front surface using a rotary tool operating at a rotary speed on the order of at least 60,000 revolutions per minute (rpm) until said back surface is thinned to 200 microns or less, the thinning being restricted to a single integrated circuit thereby maintaining structural integrity of the wafer.

13. The method as defined by claim 12 wherein step b) uses a 150 grit diamond 0.125 inch diameter diamond end mill grinding tool traveling at 3 inches per minute and taking 0.00025 inch of silicon each pass over the wafer in the presence of a constant flow of coolant.

14. The method as defined by claim 13 and further including the steps of c) removing swirl marks on the back surface after step b), and d) polishing the back surface with a polish paste.

15. The method as defined by claim 14 wherein step c) uses 400 grit diamond end mill of 0.125 inch diameter traveling at 3 inches per minute and taking 0.0001 inch cuts in depth, and step d) uses 1 micron diamond paste with a buffing wheel at 2,400 rpm.

16. The method as defined by claim 15 wherein step d) further uses 0.1 micron diamond paste and then 0.05 micron diamond paste.

* * * * *